United States Patent
Nestler et al.

(10) Patent No.: US 7,026,503 B2
(45) Date of Patent: Apr. 11, 2006

(54) METHOD FOR PRODUCING (METH)ACRYLIC ACID ESTERS

(75) Inventors: Gerhard Nestler, Vienna (AT); Ulrich Rauh, Limburgerhof (DE); Jürgen Schröder, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 88 days.

(21) Appl. No.: 10/478,695

(22) PCT Filed: May 28, 2002

(86) PCT No.: PCT/EP02/05821

§ 371 (c)(1),
(2), (4) Date: Dec. 8, 2003

(87) PCT Pub. No.: WO02/100815

PCT Pub. Date: Dec. 19, 2002

(65) Prior Publication Data

US 2004/0158096 A1     Aug. 12, 2004

(30) Foreign Application Priority Data

Jun. 8, 2001    (DE) ................... 101 27 941

(51) Int. Cl.
*C07C 67/02* (2006.01)
(52) U.S. Cl. ................................. 560/217
(58) Field of Classification Search ........... 560/217
See application file for complete search history.

(56) References Cited

U.S. PATENT DOCUMENTS

| | | |
|---|---|---|
| 2,406,561 A | 8/1946 | Rehberg |
| 3,868,410 A | 2/1975 | Horlenko et al. |
| 4,280,010 A | 7/1981 | Erpenbach et al. |

FOREIGN PATENT DOCUMENTS

| | | |
|---|---|---|
| BR | 8 701 337 | 9/1988 |
| CN | 1 058 390 | 2/1992 |
| CN | 1 063 678 | 8/1992 |
| DE | 2 008 618 | 9/1970 |
| DE | 2 145 283 | 7/1972 |
| DE | 2 317 226 | 10/1974 |
| DE | 23 23 328 | 4/1982 |
| DE | 195 47 485 | 5/1996 |
| DE | 195 47 459 | 7/1996 |
| DE | 195 10 891 | 9/1996 |
| DE | 195 36 178 | 4/1997 |
| DE | 196 04 252 | 8/1997 |
| DE | 196 04 253 | 8/1997 |
| DE | 197 01 737 | 7/1998 |
| DE | 198 51 983 | 5/2000 |
| EP | 0 143 639 | 6/1985 |
| EP | 0 160 427 | 11/1985 |
| EP | 0 298 867 | 1/1989 |
| EP | 0 210 907 | 9/1989 |
| EP | 0 736 510 | 10/1996 |
| EP | 0 906 902 | 4/1999 |
| EP | 0 960 877 | 12/1999 |
| WO | 99/23060 | 5/1999 |
| WO | 00/27789 | 5/2000 |

OTHER PUBLICATIONS

Kirk Othmer Encyclopedia of Chem. Technology, 4$^{th}$ Ed., pp. 301-302 1994.
Ullmann's Encyclopedia of Industrial Chem., 6$^{th}$ Ed., Electronic Release, "Acrylic Acid and Derivatives-Esterification" 1999.
Organikum, vol. 17 Veb Deutscher Verlag Der Wissenschaften, Berlin, p. 506 1988.

*Primary Examiner*—Paul A. Zucker
(74) *Attorney, Agent, or Firm*—Oblon, Spivak, McClelland, Maier & Neustadt, P.C.

(57) ABSTRACT

Higher (meth)acrylates IV are prepared by transesterification of a lower (meth)acrylate I with a higher alcohol $R^2OH$ in the presence of a stabilizer or stabilizer mixture and of a catalyst or catalyst mixture, by a process in which the liberated lower alkanol $R^1OH$ is separated off and is fed at least partly to the preparation of the lower (meth)acrylate I.

24 Claims, No Drawings

METHOD FOR PRODUCING (METH)ACRYLIC ACID ESTERS

The present invention relates to a process for the preparation of higher (meth)acrylates by esterification of a lower (meth)acrylate with a higher alkanol and recycling of the liberated lower alcohol to the process for the preparation of the lower (meth)acrylate.

(Meth)acrylates are useful starting compounds for the preparation of polymers and copolymers which are used, for example, as finishes, dispersions or adhesives.

In this application, the terms (meth)acrylic acid and (meth)acrylate refer to methacrylic acid and acrylic acid, and methacrylate and acrylate, respectively.

Kirk Othmer, Encyclopedia of Chemical Technology, 4th Ed., 1994, pages 301–302, describes a preparation of lower acrylates by esterification, in which acrylic acid, alkanol and catalyst, e.g. sulfuric acid, are reacted using recycled streams in a reactor with connected distillation column, in which the desired ester, excess alkanol and the water formed during the reaction are separated off via the top. The phases in the distillate are separated and a part of the organic phase is added as reflux to the distillation column, but the major part is fed to a wash tower in which alkanol and acrylic acid are removed by washing. If required, base may be added to this wash process to remove traces of acrylic acid. The water-containing ester is then freed from water by distillation and purified by distillation in a further distillation column, and once again the phases are separated in the distillate. The high boilers remaining behind are passed into a stripping apparatus, and useful products are separated off and recycled.

The aqueous phases obtained in the process and originating from the distillate in the elimination of water, the refined fraction in the washing and the aqueous phase of the distillate of the distillation column connected to the reactor are combined and the alkanol and acrylate contained therein are separated off in an alcohol stripper and are recycled to the reactor.

Furthermore, high boilers from the esterification reactor are removed, and useful products are distilled off in a stripping apparatus and are recycled to the esterification reactor.

In the case of the esterification with butanol, the alkanol is removed as an azeotropic butanol/butyl acrylate mixture using a further azeotrope column and is recycled to the reactor.

In Ullmann's Encyclopedia of Industrial Chemistry, 6th ed, 1999 Electronic Release, Chapter: Acrylic Acid and Derivatives—Esterification, a process for the preparation of higher alkyl acrylates is described which is carried out in the presence of an organic solvent as an entraining agent and sulfuric acid as a catalyst. The water formed in the reaction is removed by means of azeotropic distillation.

The reaction mixture removed from the reactor is neutralized with alkali and separated into an aqueous phase and an organic phase. The organic phase is freed from the organic solvent used and from the alkanol in two distillation columns, and the crude ester thus obtained is then purified by distillation.

The aqueous phases obtained in the process are combined, and organic material contained therein is separated off and is recycled to the reaction.

From these two processes, it is evident that (meth)acrylic acid can be separated from the corresponding ester by treatment with a base.

DE-C2 232 33 28 describes a process for the extractive separation of the unconverted acrylic acid from the esterification waste liquors which are obtained in the esterification of acrylic acid with alkanols, such as n-butanol, isobutanol and 2-ethylhexanol, by extraction with an alkanol/alkyl acrylate mixture.

The aqueous solutions which are fed to the extraction are said to contain the acrylic acid in free form, i.e. alkaline or neutral waste liquors are expediently acidified, for example with hydrochloric or sulfuric acid, before the extraction, so that all of the acrylic acid is liberated.

When the process is carried out in practice, the amount of butanol/butyl acrylate mixture relative to aqueous acrylic acid solution can be varied within wide ranges. Butanol/butyl acrylate mixtures of said type extract acrylic acid far more effectively than do butyl acrylate and butanol by themselves.

In summary, the esterification of (meth)acrylic acid with an alkanol of 1 to 8 carbon atoms is generally acid-catalyzed, and the catalysts used are, for example, acidic or strongly acidic ion exchangers, sulfuric acid or sulfonic acids, e.g. para-toluenesulfonic acid, methanesulfonic acid, trifluoromethanesulfonic acid, benzenesulfonic acid, xylenesulfonic acid, naphthalenesulfonic acid or dodecylbenzenesulfonic acid. Up to 20% by weight of catalyst may be used, cf. for example DE-A 195 10 891.

The (meth)acrylic acid used can, for example, be purified beforehand, but it may also be a crude (meth)acrylic acid, as described, for example, in DE-A 198 51 983. A cascade may be an expedient reactor, cf. for example DE-A 195 36 178.

The water of reaction formed during the reaction is generally separated off by distillation, with or without the addition of an entraining agent, e.g. benzene, toluene or cyclohexane, which forms an azeotropic mixture with water, if required as an azeotropic mixture with the alkanol used. Frequently, however, the desired ester is distilled off together with the water of reaction formed during the reaction and the alkanol, cf. for example WO 99/23060 or U.S. Pat. No. 4,280,010.

As described above, the distillate which frequently contains (meth)acrylic acid is generally separated into an organic phase and an aqueous phase.

The organic phase can be recycled partly or substantially completely as a reflux to the distillation column, but it is generally subjected at least partly to a separation operation in which the starting alkanol is separated from the desired ester, it being possible for the desired ester to be further purified if necessary and the alkanol to be recycled to the reaction.

The aqueous phase can be recycled at least partly as a reflux to the column, but it may also be directly discharged or subjected to a further working-up in which useful products present are separated off.

The reaction mixture removed from the reaction zone is generally fed to a separation zone which usually has at least one rectification unit. If required, extraction is effected beforehand with a suitable solvent, e.g. water, in order to separate off (meth)acrylic acid and/or catalyst. In the separation zone, further phase separations between an organic phase and an aqueous phase can also be carried out, as described, for example, in DE-A 196 04 252 and DE-A 196 04 253.

Oligomers (oxyesters) obtained as high boilers in the course of the preparation and/or working-up process can be cleaved, for example thermally and in the presence of stabilizers, as described in U.S. Pat. No. 3,868,410, or in the presence of acid, e.g. dodecylbenzenesulfonic acid, cf. for example WO 00/27789, in the presence of (meth)acrylic acid or oligomeric (meth)acrylic acid, cf. for example DE-A 195 47 485 and DE-A 195 47 459, and, if required, additionally in the presence of water, cf. for example DE-A 197 01 737. This cleavage can be carried out, for example, in a reaction cascade, cf. for example CN 1 058 390 and CN 1 063 678.

The preparation of (meth)acrylates by transesterification in the presence of acidic or basic catalysts is generally known. Catalysts proposed in particular are titanium alcoholates whose alkyl groups are $C_1$–$C_4$-alkyl radicals, e.g. tetramethyl, tetraethyl, tetraisopropyl, tetra-n-propyl, tetraisobutyl and tetra-n-butyl titanate (cf. for example EP-B1 298 867, EP-A2 960 877). Other proposed catalysts include titanium phenolates (German Laid-Open Application DOS 20 08 618), metal chelate compounds of, for example, hafnium, titanium, zirconium or calcium, alkali metal and magnesium alcoholates, organic tin compounds or calcium and lithium compounds, for example oxides, hydroxides, carbonates or halides.

Since the transesterification is known to be an equilibrium reaction, one of the starting materials must be used in a large excess and/or one of the reaction products must be removed from the equilibrium in order to obtain economical conversions. As a rule, the lower alkanol $R^1OH$ (cf. equation 1) liberated during the transesterification, being the alcohol component having the lowest boiling point, is therefore removed from the equilibrium by distillation. The disadvantage here is that the liberated alkanols, usually methanol or ethanol, form an azeotropic mixture with the corresponding (meth)acrylates (methyl or ethyl (meth)acrylate) and hence cannot be separated directly by distillation.

In addition, the distillate contains at least traces of the higher alcohol $R^2OH$ and consequently also cannot be recycled directly to the process for the preparation of the lower (meth)acrylate I of the lower alkanol $R^1OH$.

For ecological and economic reasons, however, the reuse of the mixture or azeotropic mixture distilled off or of its individual components (alkanol and/or (meth)acrylate) is advantageous.

Owing to the position of the boiling points and/or the formation of azeotropic mixtures, this distillate, as stated above, generally does not consist of the pure lower alkanol but is contaminated with the lower (meth)acrylate and possibly the higher alcohol.

In the case of the preparation of dimethylaminoethyl acrylate from n-butyl acrylate and dimethylaminoethanol, for example, a distillate which predominantly comprises 5–15% by weight of n-butyl acrylate, 85–95% by weight of n-butanol and 0.01–0.5% by weight of dimethylaminoethanol is obtained.

The individual components have the following boiling points (bp.):

| | |
|---|---|
| n-Butyl acrylate | bp. 146.7° C. |
| n-Butanol | bp. 117.5° C. |
| n-Butanol/n-butyl Acrylate azeotrope | bp. 117° C. |
| Dimethylaminoethanol | bp. 133.9° C. |

Since, for the above reasons, it is desirable to utilize the distillate, contamination has an adverse effect, particularly if, as in this case, the higher alcohol is a basic compound, i.e. here an amino group. The direct recycling to the synthesis of the lower ester, which is economically particularly desirable, is thus adversely affected in particular (EP-A 906 902, page 3, lines 4 to 16).

Owing to the small boiling point difference or azeotrope formation, some of the impurities are difficult to remove and can lead to the formation of further byproducts, for example by esterification reactions or addition of the double bond of the esters.

EP-A 906 902 attempts to solve the problem caused by the basic impurities by passing the alcohol-containing distillate, either directly or after an additional distillation, over an acidic ion exchange resin. The basic, nitrogen-containing impurities are bound by the acidic groups and thus separated from the alkanol/acrylate mixture.

The process described in EP-A2 906 902 for the preparation and isolation of alkylaminoalkyl (meth)acrylates substantially comprises the following stages:

1. Batchwise transesterification in the presence of the catalyst dibutyltin oxide and of the stabilizer phenothiazine, the main amount of the alkylaminoalkanol being added after the start of the reaction in a manner such that its concentration in the reaction mixture does not exceed 25 mol %.
2. Distillative removal of the lower alkanol formed in the transesterification, as an azeotropic mixture with the lower (meth)acrylate via a column, it being possible, if necessary, for the distillate to be subjected to a further distillation.
3. Treatment of the distillate, which mainly comprises lower alkanol and lower (meth)acrylate, with an acidic cation exchanger. The basic impurities (amines) which prevent the use of the distillate in the preparation of the lower ester due to deactivation of the catalyst used, are separated off thereby.
4. Distillative separation of the reaction mixture in the transesterification into a top product, mainly comprising desired ester, lower alkanol and starting materials, and a bottom product, which substantially contains catalyst, stabilizer, Michael adducts and polymers and which may be reusable in the transesterification. If the catalyst loses its activity, it is disposed of.
   Alternatively, the catalyst can be separated off in two stages, first the lower (meth)acrylate being separated off via the top of a column and recycled to the transesterification. In a second distillation column, the desired ester and remaining low boilers are separated off as top product, and the catalyst-containing bottom product is, if required, reused in a transesterification.
5. The distillate containing the desired ester is separated, in a further distillation stage, into a top product containing aminoalkanol and lower ester, which can be reused in the transesterification, and a bottom product which contains the desired ester.
6. Finally, in a further distillation step (purification by distillation), the desired ester is isolated in a purity of 99.8% from the bottom product containing the desired ester.
7. A part of the desired ester is obtained from the bottom product of the purification by distillation, which still contains the desired ester, in a distillation, preferably a thin-film distillation, and is fed to the low boiler distillation.

Among the disadvantages of the process are
that the transesterification is carried out batchwise,
that the dialkylaminoalkanol has to be added to the reactor over a long period (4 hours), that long reaction times (7–8 hours) are required, favoring the formation of byproducts and of polymer, that the azeotropic mixture has to be purified by a technically complicated procedure over an ion exchanger bed, which is environmentally polluting owing to the necessity of rinsing, that the yield is low (about 33%, based on dimethylaminoethanol used, cf. example III-1 in EP-A2 906 902) and that the residues are not worked up to recover useful products.

EP-A2 960 877 describes a continuous process for the preparation of dialkylaminoalkyl (meth)acrylates by transesterification of methyl or ethyl (meth)acrylate with dialkylaminoalkanols in the presence of tetraethyl, tetrabutyl or tetra(2-ethylhexyl) titanate. The transesterification there is carried out in a stirred reactor and the working-up of the reaction mixture is effected in the following steps:

1. The reaction mixture is separated in a distillation unit into a top product, which substantially contains the desired ester and the low boilers, and a bottom product, which mainly comprises high boilers, catalyst and a little desired ester.
2. The bottom product can, if required, be purified in a thin-film evaporator, the distillate being recycled to the transesterification. The catalyst-containing bottom product is discharged.
3. The top product containing the desired ester is separated in a further distillation unit into a low boiler fraction, which is recycled to the reactor, and a bottom product, predominantly desired ester.
4. In a further distillative purification step, the desired ester is isolated (purity 99.8%) as top product from the bottom product. The resulting residue is recycled to the low boiler removal.

This process has, inter alia, the following disadvantages:
The transesterification is carried out in a stirred reactor which is likely to need repairs owing to its moving parts
The alkanol component of the catalyst leads to impurities (cf. EP-A2 960 877, page 2, lines 49 to 50)
No utilization of the distillate separated off in the reactor and hence a loss of useful products
No utilization of the resulting high boilers (e.g. Michael adducts)

In order to avoid in general the formation of a distillate or azeotropic mixture which consists of the lower alkanol and the corresponding (meth)acrylate in the transesterification, various patents (e.g. U.S. Pat. No. 2,406,561, German Laid-Open Application DOS 2 145 283, EP-B1 210907) propose the use of assistants which form heteroazeotropes with the lower alkanols liberated, e.g. hexane, cyclohexane or benzene.

The lower alkanol liberated during the transesterification is separated off by distillation as an azeotropic mixture with the assistant, the condensate being separated into two phases. The phase which contains the assistant is recycled to the transesterification and the alkanol phase saturated with assistant is discharged. However, this alkanol phase must be separated from the residual assistant before further utilization. German Laid-Open Application DOS 2 145 283 proposes, for example, the separation of the benzene/alkanol azeotropic mixture by means of molecular sieves. Such a process is complicated and is not economical on an industrial scale.

DE-A 23 17 226 proposes separating the azeotropic mixture formed from alkanol and the corresponding (meth) acrylate by treatment with water, the alkanol being washed out. The process is not economical since an aqueous alkanol solution forms and has to be disposed of or worked up, and the ester phase has to be dried before recycling to the transesterification.

EP-A2 143 639 recommends the separation of these azeotropic mixtures using complex-forming salts, e.g. LiCl, and an extracting agent. The process is uneconomical since it produces wastewater and requires a plurality of distillation steps.

EP-A1 736 510 proposes carrying out the separation of the azeotropic mixture comprising methyl (meth)acrylate and methanol and possibly water by distillation in the presence of a solvent which forms an azeotropic mixture with methanol, e.g. pentane, hexane, heptane or 2,3-dimethylbutane.

However, the use of an additional assistant makes this process, too, uneconomical.

Transesterification processes in which no azeotropic mixture is formed have also been proposed.

EP-A2 160 427 proposes, for example, a transesterification in the absence of free higher alcohol. There, the lower (meth)acrylate is reacted with the titanium alcoholate of the higher alcohol, the titanate of the lower alkanol being formed in addition to the desired ester and being reacted in a separate reaction step with the higher alcohol to give the corresponding titanate again. Because of the large amounts of titanate required, this process is of no commercial importance.

A further problem in the transesterification is the formation of Michael adducts. Here, Michael adducts are understood as meaning the compounds formed by addition of the alcohols at the double bond of the (meth)acrylates (EP-A2 906 902, pages 8 to 9).

It is generally known that this addition (cf. equation 2) takes place in particular in the presence of alkaline catalysts (Organikum, 17th Edition, page 506, VEB Deutscher Verlag der Wissenschaften, Berlin 1988).

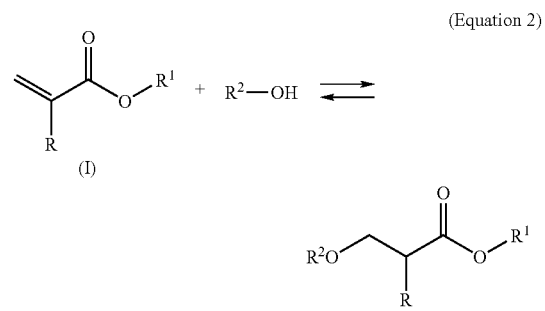
(Equation 2)

In the transesterification according to equation 1, the adducts (II) and (III) play a substantial role

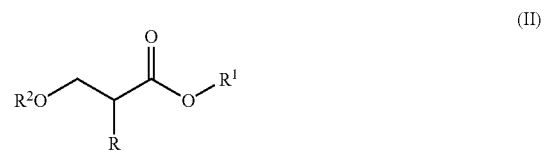
(II)

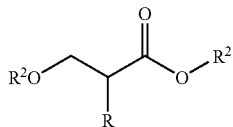

(III)

The results of this adduct formation are lower yields and a more complicated distillation for obtaining the desired ester in high purity.

The formation of the adducts according to the general equation 2 can, as is generally known, be reduced by minimizing the concentration of free alkanol. EP-A2 906 902 therefore proposes continuously adding the main amount of the alkanol during the transesterification and not allowing the concentration of free alkanol to increase above 25 mol %.

It is an object of the present invention to provide a process for the preparation of higher (meth)acrylates by transesterification of lower (meth)acrylates, in which the lower alcohol liberated can be reused in the preparation of the lower (meth)acrylate without additional process engineering steps.

We have found that this object is achieved and that higher (meth)acrylates IV can be prepared by transesterification of a lower (meth)acrylate I with a higher alcohol $R^2OH$ in the presence of a stabilizer or stabilizer mixture and of a catalyst or catalyst mixture, if the lower alkanol $R^1OH$ liberated is separated off and is at least partly fed to the preparation of the lower (meth)acrylate I.

The lower alkanol $R^1OH$ liberated during the transesterification can be fed to the preparation of the lower (meth) acrylate I without further purification.

It is preferably used for reextraction of (meth)acrylic acid from aqueous phases obtained in the working-up process, particularly preferably in the aqueous phase which is obtained by separating off the excess (meth)acrylic acid from the esterification mixture.

The lower alkanol $R^1OH$ liberated during the transesterification is preferably separated off by distillation.

The novel process is generally carried out as follows:

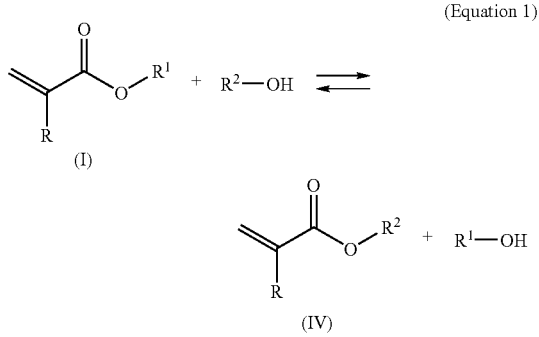

(Equation 1)

$R^1$, $R^2$ and $R^3$ may each be aromatic, aliphatic or cycloaliphatic, straight-chain or branched, saturated or unsaturated and may contain heteroatoms or aromatic substituents.

The radicals preferably comprise:
$R^1=C_1-C_4$-alkyl
R=H or $CH_3$
$R^2=C_2-C_{12}$-alkyl, substituted by at least one $NR^3_2$ group, where $R^3$ may be identical or different.
$R^3=C_1-C_6$-alkyl, where N may also be a member of a five- to seven-membered ring.

$R^1$ should contain at least one carbon atom less than $R^2$.

$R^1$ is, for example, methyl, ethyl, n-propyl, isopropyl, n-butyl, isobutyl, 2-butyl or tert-butyl, preferably n-butyl or isobutyl.

$R^2$ is, for example,
2-(dimethylamino)ethyl, 3-(dimethylamino)propyl, 4-(dimethylamino)butyl, 5-(dimethylamino)pentyl, 6-(dimethylamino)hexyl, 8-(dimethylamino)octyl, 10-(dimethylamino)decyl, 12-(dimethylamino)dodecyl, 2-(diethylamino)ethyl, 3-(diethylamino)propyl, 4-(diethylamino)butyl, 5-(diethylamino)pentyl, 6-(diethylamino)hexyl, 8-(diethylamino)octyl, 10-(diethylamino)decyl, 12-(diethylamino)dodecyl, 2-(di(isopropyl)amino)ethyl, 3-(di(isopropyl)amino)propyl, 4-(di(isopropyl)amino)butyl, 5-(di(isopropyl)amino)pentyl, 6-(di(isopropyl)amino)hexyl, 8-(di(isopropyl)amino)octyl, 10-(di(isopropyl)amino)decyl, 12-(di(isopropyl)amino)dodecyl, 2-(dibutylamino)ethyl, 3-(dibutylamino)propyl, 4-(dibutylamino)butyl, 5-(dibutylamino)pentyl, 6-(dibutylamino)hexyl, 8-(dibutylamino)octyl, 10-(dibutylamino)decyl, 12-(dibutylamino)dodecyl, 2-(dihexylamino)ethyl, 3-(dihexylamino)propyl, 4-(dihexylamino)butyl, 5-(dihexylamino)pentyl, 6-(dihexylamino)hexyl, 8-(dihexylamino)octyl, 10-(dihexylamino)decyl, 12-(dihexylamino)dodecyl, 2-(methylethylamino)ethyl, 2-(methylpropylamino)ethyl, 2-(methylisopropylamino)ethyl, 2-(methylbutylamino)ethyl, 2-(methylhexylamino)ethyl, 2-(methyloctylamino)ethyl, 2-(ethylpropylamino)ethyl, 2-(ethylisopropylamino)ethyl, 2-(ethylbutylamino)ethyl, 2-(ethylhexylamino)ethyl, 2-(ethyloctylamino)ethyl, 3-(methylethylamino)propyl, 3-(methylpropylamino)propyl, 3-(methylisopropylamino)propyl, 3-(methylbutylamino)propyl, 3-(methylhexylamino)propyl, 3-(methyloctylamino)propyl, 3-(ethylpropylamino)propyl, 3-(ethylisopropylamino)propyl, 3-(ethylbutylamino)propyl, 3-(ethylhexylamino)propyl, 3-(ethyloctylamino)propyl, 4-(methylethylamino)butyl, 4-(methylpropylamino)butyl, 4-(methylisopropylamino)butyl, 4-(methylbutylamino)butyl, 4-(methylhexylamino)butyl, 4-(methyloctylamino)butyl, 4-(ethylpropylamino)butyl, 4-(ethylisopropylamino)butyl, 4-(ethylbutylamino)butyl, 4-(ethylhexylamino)butyl, 4-(ethyloctylamino)butyl, 2-(N-piperidinyl)ethyl, 3-(N-piperidinyl)propyl, 4-(N-piperidinyl)butyl, 5-(N-piperidinyl)pentyl, 6-(N-piperidinyl)hexyl, 8-(N-piperidinyl)octyl, 10-(N-piperidinyl)decyl, 12-(N-piperidinyl)dodecyl, 2-(N-pyrrolidinyl)ethyl, 3-(N-pyrrolidinyl)propyl, 4-(N-pyrrolidinyl)butyl, 5-(N-pyrrolidinyl)pentyl, 6-(N-pyrrolidinyl)hexyl, 8-(N-pyrrolidinyl)octyl, 10-(N-pyrrolidinyl)decyl, 12-(N-pyrrolidinyl)dodecyl, 2-(N-morpholino)ethyl, 3-(N-morpholino)propyl, 4-(N-morpholino)butyl, 5-(N-morpholino)pentyl, 6-(N-morpholino)hexyl, 8-(N-morpholino)octyl, 10-(N-morpholino)decyl, 12-(N-morpholino)dodecyl, 2-(N'-methyl-N-piperazinyl)ethyl, 3-(N'-methyl-N-piperazinyl)propyl, 4-(N'-methyl-N-piperazinyl)butyl, 5-(N'-methyl-N-piperazinyl)pentyl, 6-(N'-methyl-N-piperazinyl)hexyl, 8-(N'-methyl-N-piperazinyl)octyl, 10-(N'-methyl-N-piperazinyl)decyl, 12-(N'-methyl-N-piperazinyl)dodecyl, 2-(N'-ethyl-N-piperazinyl)ethyl, 3-(N'-ethyl-N-piperazinyl)propyl, 4-(N'-ethyl-N-piperazinyl)butyl, 5-(N'-ethyl-N-piperazinyl)pentyl, 6-(N'-ethyl-N-piperazinyl)hexyl, 8-(N'-ethyl-N-piperazinyl)octyl, 10-(N'-ethyl-N-piperazinyl)decyl, 12-(N'-ethyl-N-piperazinyl)dodecyl, 2-(N'-isopropyl-N-piperazinyl)ethyl, 3-(N'-isopropyl-N-piperazinyl)propyl, 4-(N'-isopropyl-N-piperazinyl)butyl, 5-(N'-isopropyl-N-piperazinyl)pentyl, 6-(N'-isopropyl-N-piperazinyl)hexyl, 8-(N'-isopropyl-N-piperazinyl)octyl, 10-(N'-isopropyl-N-piperazinyl)decyl or 12-(N'-isopropyl-N-piperazinyl)dodecyl.

Furthermore, $R^2OH$ may be ethoxylated and/or propoxylated alcohols or mixed ethoxylated/propoxylated aminoalcohols $R^3{}_2N(\!\!-\!\!CH_2CH_2\!\!-\!\!O)_y\!\!-\!\!H$ or
$R^3{}_2N(\!\!-\!\!CH(CH_3)\!\!-\!\!CH_2\!\!-\!\!O)_y\!\!-\!\!H$ or $R^3{}_2N(\!\!-\!\!CH_2\!\!-\!\!CH(CH_3)\!\!-\!\!O\!\!-\!\!)_y\!\!-\!\!H$, where y is an integer from 1 to 4.

Dialkylaminoethanols are preferably used, dimethylaminoethanol, diethylaminoethanol and di-n-butylaminoethanol being particularly preferred.

The transesterification of the lower (meth)acrylate (I) with the higher alkanol $R^2OH$ is carried out in the presence of a catalyst or a catalyst mixture in a manner known per se, for example by one of the processes mentioned at the outset.

Typical conditions under which the transesterification can take place are, for example:

| | |
|---|---|
| lower (meth)acrylate:higher alcohol $R^2OH$ = | 1–4:1 (molar) |
| Amount of catalyst in the reaction mixture = | 0.5–5% by weight |
| Amount of stabilizer in the reaction mixture = | 0.05–0.5% by weight |
| Reaction temperature = | 60–160° C. |
| Duration of reaction = | 1–10 hours |

The reaction can be carried out under atmospheric, superatmospheric or reduced pressure, preferably at atmospheric pressure or under slightly reduced pressure (300–800 mbar absolute).

The transesterification can be carried out, for example, continuously, semicontinuously or batchwise, preferably continuously.

Examples of stabilizers used are N-oxyls, e.g. 4-hydroxy-2,2,6,6-tetramethylpiperidin-N-oxyl or 4-oxo-2,2,6,6-tetramethylpiperidin-N-oxyl, phenols and naphthols, e.g. p-aminophenol, p-nitrosophenol, 2-tert-butylphenol, 4-tert-butylphenol, 2,4-di-tert-butylphenol, 2-methyl-4-tert-butylphenol, 4-methyl-2,6-di-tert-butylphenol (2,6-di-tert-butyl-p-cresol) or 4-tert-butyl-2,6-dimethylphenol, quinones, e.g. hydroquinone or hydroquinone monomethyl ether, aromatic amines, e.g. N,N-diphenylamine, phenylenediamines, e.g. N,N'-dialkyl-para-phenylenediamine, it being possible for the alkyl radicals to be identical or different and, independently of one another, each to consist of 1 to 4 carbon atoms and to be straight-chain or branched, e.g. N,N'-dimethyl-para-phenylenediamine or N,N'-diethyl-para-phenylenediamine, hydroxylamines, e.g. N,N-diethylhydroxylamine, phosphorus-containing compounds, e.g. triphenylphosphine, triphenyl phosphite or triethyl phosphite, or sulfur-containing compounds, e.g. diphenyl sulfide or phenothiazine, or mixtures thereof.

Furthermore, they may also be degradation products or derivatives of stabilizers, for example the Michael adduct of (meth)acrylic acid or (meth)acrylates and hydroquinone.

Stabilization can be effected in the presence or absence of molecular oxygen.

Preferably, the stabilization is effected using phenothiazine, hydroquinone, hydroquinone monomethyl ether, 4-hydroxy-2,2,6,6-tetramethylpiperidin-N-oxyl, 4-oxo-2,2,6,6-tetramethylpiperidin-N-oxyl, 2,6-di-tert-butyl-p-cresol or mixtures thereof in amounts of, in each case, from 10 to 5000 ppm.

The addition can be carried out in each case via the starting materials or via the recycle or reflux streams.

In a particularly preferred manner, the dissolved stabilizer mixture is sprayed onto condenser surfaces.

The catalysts used may be the known transesterification catalysts mentioned at the outset, preferably tetraalkyl titanates, alkali metal or alkaline earth metal alcoholates or metal chelates, particularly preferably tetraalkyl titanates and very particularly preferably the tetraalkyl titanates of the alcohols participating in the reaction, e.g. $Ti(OR^1)_4$ or $Ti(OR^2)_4$.

If a titanium alcoholate $Ti(OR^2)_4$ is used, it can be prepared, for example, as follows before use in the transesterification:

A titanium alcoholate $Ti(OR^4)_4$ of a lower alcohol, preferably the isopropylate, isobutylate or n-butylate, is reacted with the higher alcohol $R^2OH$ (cf. equation 3) at elevated temperatures (50–130° C.). The higher alcohol is used in a molar excess (from 1:5 to 1:20). The lower alcohol $R^4OH$ is removed by distillation during the reaction.

$$Ti(OR^4)_4 + R^2OH \rightleftharpoons Ti(OR^2) + R^4OH \qquad \text{Equation 3}$$

For $R^2$, cf equation (1)

$R^4$ is $C_1$–$C_8$-alkyl, preferably isopropyl, isobutyl or n-butyl $R^2OH$ and $R^4OH$ should preferably fulfill the following condition with regard to their boiling points bp.:

$bp.\ (R^2OH) \geq bp.\ (R^4OH) + 20°\ C.$

Under these conditions, it is technically simple to keep the losses of $R^2OH$ low and to separate off $R^4OH$ as completely as possible.

The alkanol $R^4OH$ formed in the reaction is separated off by distillation or rectification, if required under reduced pressure. This can, if required, be supported by stripping with a suitable unreactive gas. The resulting residue is a catalyst solution for transesterification (Ti content: 1–10% by weight) and as a rule contains less than 400 ppm of $R^4OH$. Thus, virtually no foreign alkanol ($R^4OH$) is introduced into the transesterification mixture and, as a rule, the content in the mixture is less than 100 ppm.

However, it is of course also possible for mixed titanium alcoholates to be present in the catalyst solution, depending on the transesterification according to equation 3.

Transesterification

The lower (meth)acrylate I used has, as a rule, the following composition:

99.0–99.95% by weight (meth)acrylate
0.001–0.1% by weight acetic ester
0.02–0.1% by weight propionic ester
0.001–0.05% by weight water Furthermore, the lower alkanol $R^1OH$, its dialkyl ether, (meth)acrylic acid and other, for example isomeric (meth)acrylates may be present.

The higher alcohol $R^2OH$ usually has a purity of not less than 99.0% by weight and a water content of 0.01–0.2% by weight.

The content of ethylene glycol in the higher alcohol $R^2OH$ should not be more than 100 ppm, preferably not more than 50 ppm, particularly preferably not more than 20 ppm, in particular not more than 10 ppm. The content of vinyloxyethanol in the higher alcohol $R^2OH$ should be not more than 100 ppm, preferably not more than 50 ppm, particularly preferably not more than 20 ppm, in particular not more than 10 ppm.

Mixtures of higher alkanols may also be used for the transesterification.

The lower (meth)acrylate I is reacted with the higher alkanol $R^2OH$ in a molar ratio of from 1:1 to 4:1 in the presence of at least one of the catalysts described above.

The transesterification is carried out in a reactor or a plurality of reactors, preferably in one reactor or two reactors connected in series, having at least one attached rectification column and, if required, condensers of conventional design. In a cascade, each reactor may have a distillation or rectification column or the vapor phases of a plurality of reactors are passed into at least one common distillation or rectification column.

Within a cascade, the temperature in the individual containers can be identical or different; preferably, it increases in the course of the cascade. The pressure, too, may be identical or different in the course of the cascade; it preferably decreases.

In general, the reaction temperature is 60–160° C., preferably 80–140° C., particularly preferably 100–130° C., and the total residence time is 1–10, preferably 1–8, particularly preferably 2–6, in particular 2–4, hours.

The reaction zone can preferably be flushed continuously with a gas or gas mixture which is inert under the reaction conditions, e.g. nitrogen, air, nitrogen/oxygen mixtures, argon, helium, carbon dioxide or carbon monoxide. Particularly preferably, the purge gas is passed along the heat exchanger surfaces present, in particular in a pumped or natural circulation present, as described in the German Patent Application with the file reference DE 101 27 938.8.

A further preferred embodiment of the transesterification may comprise feeding the reaction mixture continuously into a downstream reactor which is connected on the gas side to the transesterification reactor or the attached column, as described in the same document.

The temperature in the downstream reactor is 1–10° C. higher than in the reactor.

The rectification columns are of a known design and have internals having separation activity (e.g. bubble trays, Thormann trays, valve trays, sieve trays or dual-flow trays) or contain dumped or stacked packings. The column(s) attached to the reactor(s) has/have as a rule 10–30 theoretical plates. The reflux ratio is as a rule 5–15:1, preferably 7–12:1. The condensers are likewise of a known design, e.g. tubular or plate heat exchangers.

The uniform thorough mixing of the reaction solution is effected in a known manner, for example by stirring, pumped circulation or natural circulation. The heat can be supplied, for example, via double-jacket heating and/or external or internal heat exchangers, e.g. tube-bundle or plate heat exchangers.

The lower alkanol liberated during the transesterification is removed from the reaction zone in vapor form via an attached distillation column and, if required, is condensed with the aid of a conventional condenser, for example a tube-bundle or plate condenser. The cooling medium used may be, for example, water, air or brine.

The process is preferably carried out by separating off the lower alkanol $R^1OH$ liberated in the transesterification, substantially together with lower (meth)acrylate I and possibly higher alcohol $R^2OH$.

The distillation conditions for this purpose are established so that the alkanol content in the condensate is 20–40% by weight in the case of methanol, 30–65, preferably 40–60, % by weight in the case of ethanol and 70–95, preferably 80–90, % by weight in the case of n-butanol. As a rule, not more than 1, preferably not more than 0.5, particularly preferably not more than 0.3, % by weight of the higher alcohol $R^2OH$ are contained.

In a particularly preferred embodiment, the distillation conditions, for example theoretical plates and reflux ratio, are chosen so that a nonazeotropic mixture is taken off at the top of the column, in which mixture the content of lower (meth)acrylate is higher compared with the azeotropic composition comprising lower alkanol and lower (meth)acrylate.

The condensate can be stabilized using a solution of at least one stabilizer (see above) in the abovementioned amount, preferably by spraying onto the condenser surfaces.

A part of the distillate, for example 50–95% by weight, can be recycled as reflux to the distillation column, and the remaining part, for example from 5 to 50% by weight, is fed, according to the invention, to the preparation of the lower alkyl (meth)acrylate. Preferably, from 60 to 95, particularly preferably from 80 to 95, % by weight are added as reflux to the distillation column and from 5 to 40, particularly preferably from 5 to 20, % by weight are fed to the preparation of the lower alkyl (meth)acrylate.

Of course, the distillate in vapor form can be passed, even without condensation or after only partial condensation, into the preparation of the lower alkyl (meth)acrylate.

The distillate separated off during the transesterification can be fed continuously to a process for the preparation of the lower alkyl (meth)acrylate; particularly preferably, it is fed to the working-up process, but it can also be collected separately and fed in batchwise or semicontinuously.

For example, the distillate separated off during the transesterification can be fed directly into the esterification reaction for the preparation of the lower alkyl (meth)acrylate. Since this is generally acid-catalyzed, the small amount of the higher, basic alcohol is protonated and then no longer participates in the esterification reaction. This feed is preferred if only a very small amount of higher alkanol is present in the distillate, for example less than 1, preferably less than 0.5, particularly preferably less than 0.3, % by weight.

A working-up process is understood as meaning the measures which are required for purifying the lower (meth) acrylate after leaving the reaction zone together with any attached distillation column. This comprises, for example, distillation, rectification and extraction steps.

The distillate originating from the transesterification can, for example,
- be fed to a rectification process in which the lower alkanol $R^1OH$ is separated from the lower (meth)acrylate, for example the separation of low boilers from the esterification mixture freed from the acids in the preparation of the lower (meth)acrylate, or
- a wash process, for example for removing lower alkanol, (meth)acrylic acid and/or acidic esterification catalyst from an organic phase by means of an aqueous phase, e.g. water or alkali solution, or
- be used for the back-extraction of (meth)acrylic acid from aqueous phases obtained in the working-up process, for example from an aqueous phase, e.g. an esterification waste liquor which is obtained on separating (meth) acrylic acid from the esterification mixture or an aqueous phase which is obtained after phase separation of the distillate in a distillation within the working-up process.

The working-up process of the esterification can of course also be carried out in the presence of an assistant for the azeotropic distillation, for example benzene, toluene or cyclohexane.

The aqueous phases used for the back-extraction can advantageously be acidified, for example with sulfuric acid, before the back-extraction.

The aqueous phases remaining after the washing or the back-extraction can be further worked up, for example repeatedly subjected to the novel process or distilled or stripped for separating off lower alcohol or other useful products contained therein, or disposed of in a conventional manner.

The distillate originating from the transesterification is preferably used for the back-extraction of (meth)acrylic acid from aqueous phases which are obtained in the working-up process of the esterification and may have been combined, particularly preferably in the back-extraction of (meth) acrylic acid from wash water resulting during the treatment of the esterification reactor discharge with an aqueous phase.

For this purpose, one part by weight of the aqueous phase to be extracted is treated with, for example, from 0.1 to 5, preferably from 0.1 to 3, particularly preferably from 0.15 to 2, in particular from 0.2 to 1.5, parts by weight of the distillate originating from the transesterification.

The distillate can be used as such for the back-extraction, but lower alkanol $R^1OH$ and/or lower alkyl (meth)acrylate I can also be added, so that the mixing ratio in the extracting agent is substantially 1 to 20 parts by weight of lower alkanol to 1 to 5 parts by weight of lower alkyl (meth) acrylate. Such an addition to the distillate originating from the transesterification is generally advantageous when the content of lower alkyl (meth)acrylate is less than 30% by weight.

The extraction is carried out in general at temperatures between the highest melting point and the lowest boiling point of the components present in the system, for example at from 0 to 80° C., preferably from 0 to 60° C., particularly preferably from 10 to 50° C.

In terms of process engineering, all known extraction processes and extraction apparatuses may be used for an extraction according to the novel process, for example those which are described in Ullmann's Encyclopedia of Industrial Chemistry, 6th ed, 1999 Electronic Release, Chapter: Liquid—Liquid Extraction—Apparatus. For example, the extraction may be a one-stage or multistage, preferably multistage, extraction or one effected by the cocurrent or countercurrent procedure, preferably the countercurrent procedure.

Sieve tray columns, columns containing stacked or dumped packings, mixer-settler apparatuses and columns having rotating internals are preferably used.

In a further preferred embodiment, any desired (meth) acrylic acid-containing organic esterification mixture obtained in the preparation of the lower alkyl (meth)acrylate is mixed with at least a part of the organic phase of the distillate obtained during the transesterification which was not used as reflux for the distillation column. This can be effected, for example, before or during washing of the (meth)acrylic acid-containing stream with water and/or aqueous alkali solution.

In a further preferred embodiment, the wastewaters of this acid separation which, if required, may also be carried out several times, can be combined and acidified (pH<3), for example with 20–60% strength sulfuric acid. According to the invention, the (meth)acrylic acid can then be extracted in accordance with DE 23 23 328 with a mixture of lower alcohol and lower alkyl (meth)acrylate, e.g. butanol and butyl acrylate, this back-extraction being effected according to the invention at least partly with the distillate originating from the transesterification.

The (meth)acrylic acid-containing organic phase (extract) is fed directly to a reactor, preferably the first reactor, of the reaction zone of the esterification process, preferably via any attached distillation column, the feed preferably being effected in the lower half of the column.

The resulting wastewaters of the preparation process of the esterification can be combined and the lower alcohol dissolved therein can be recovered by stripping with steam or by distillation and/or can be disposed of.

The further working-up of the reaction mixture of the transesterification has substantially no effect on the novel process.

It can be carried out, for example, as described in the German Patent Applications with the file references DE 101 27 939.6 and DE 101 27 938.8.

According to the invention, the preparation of the lower (meth)acrylate is not limited and can be carried out, for example, by one of the processes mentioned at the outset, for example according to DE-A1 198 51 983. The process described there substantially comprises washing the reactor discharge of an esterification reaction, substantially composed of desired ester, (meth)acrylic acid, low boilers, catalyst and oxyesters, with water and/or aqueous alkali solution, the catalyst and the unconverted (meth)acrylic acid being separated off substantially completely.

Dialkylaminoalkyl (meth)acrylates prepared according to the invention, in particular dialkylaminoethyl (meth)acrylates and especially dimethylaminoethyl (meth)acrylates, are useful monomers for the preparation of copolymers. They are used as monomers in the polymerization in the present form or after quaternization.

Conventional quaternizing agents are, for example, benzyl halides, e.g. benzyl chloride, alkyl halides, e.g. methyl chloride, ethyl chloride, methyl bromide, ethylene dichloride or allyl chloride, alkylene oxides, e.g. ethylene oxide, propylene oxide, styrene oxide, isobutylene oxide or vinyloxirane, preferably ethylene oxide or propylene oxide, particularly preferably ethylene oxide, alkyl phosphites or phosphonates, e.g. trimethyl phosphite or triethyl phosphite, dialkyl sulfates, e.g. dimethyl sulfate or diethyl sulfate, dialkyl carbonates, e.g. dimethyl carbonate, diethyl carbonate or di-n-butyl carbonate, chlorohydrin or epichlorohydrin.

In particular, those copolymers which contain the quaternized monomers incorporated as polymerized units are used in water treatment, for example as ion exchange resins or as a component of membranes.

The examples which follow illustrate the novel process without restricting it.

ppm and percentages used in this document are percentages by weight and ppm by weight, unless stated otherwise.

EXAMPLE 1

Transesterification Example

A mixture of 3600 g of n-butyl acrylate, 1500 g of dimethylaminoethanol, 100 g of titanium tetra-n-butylate, 3 g of hydroquinone monomethyl ether and 1 g of phenothiazine was heated to the boil in a 10 l stirred reactor having an attached packed column (height 150 cm, diameter 2.8 cm, 0.5 cm Raschig rings as packing) and condenser. The n-butanol liberated was separated off in gaseous form via the column and was condensed (top temperature 92° C., 370 mbar). 1535 g of distillate were discharged in the course of 4 hours. 100 g per hour of a solution of 1000 ppm of phenothiazine in n-butyl acrylate were added at the top of the column. The distillate had substantially the following composition:

79.5% by weight n-butanol
20.1% by weight n-butylacrylate
0.2% by weight dimethylaminoethanol According to gas chromatographic analysis, the reaction mixture (4060 g) substantially contained 56.3% by weight dimethylaminoethyl acrylate
40.1% by weight n-butyl acrylate
0.6% by weight dimethylaminoethanol
1.8% by weight n-butanol
0.8% by weight oxyester The conversion with respect to dimethylaminoethanol was 98% and the yield 95%.

EXAMPLE 2

Extraction Example

The waste liquors obtained in the course of the separation of acid from the reaction discharge in the preparation of n-butyl acrylate according to DE-A 198 51 983, example 2, were combined and were acidified with sulfuric acid (pH 1), and the acrylic acid (content 3.24% by weight) was extracted in one stage in a separating funnel at 25° C. with the distillate from example 1, separated off from the esterification reactor, or with a distillate enriched with n-butyl acrylate or with mixtures of n-butanol and n-butyl acrylate (in each case 25 g/100 g of waste liquor).

The amount of extracted acrylic acid in the waste liquor was determined.

Degree of extraction=(content of acrylic acid before extraction−content of acrylic acid after extraction)/content of acrylic acid before extraction The distillate from example 1, obtained during the transesterification of butyl acrylate with dimethylaminoethanol, had substantially the following composition:

79.5% by weight n-butanol
20.1% by weight n-butyl acrylate
0.2% by weight dimethylaminoethanol For comparison, synthetic mixtures of n-butanol and n-butyl acrylate having the following weight ratios were used:

| Extracting agent: | Degree of extraction: |
| --- | --- |
| distillate (see above) | 35% |
| distillate + n-butyl acrylate 1:0.6 | 45% |
| n-butanol:n-butyl acrylate 1:3 | 44% |
| n-butanol:n-butyl acrylate 1:1 | 45% |
| n-butanol:n-butyl acrylate 3:1 | 38% |
| n-butanol:n-butyl acrylate 4:1 | 36% |

After the extraction, no dimethylaminoethanol was detectable in the extracting agent.

EXAMPLE 3

Esterification Example

A stirred kettle cascade consisting of 3 stirred reactors which each had a reaction volume of 1 l and were equipped with column, condenser and phase separation vessel was fed in continuous operation with, per hour, 533 g of crude acrylic acid, 15 g of sulfuric acid, 510 g of n-butanol and 200 g of the mixture obtained in the back-extraction of the acrylic acid (see below). In addition, 107 g of a low boiler fraction (see below) per hour were recycled via the column of the first reactor. The crude acrylic acid contained substantially 99.3% by weight of acrylic acid, 0.2% by-weight of acetic acid, 0.03% by weight of propionic acid, 0.11% by weight of maleic anhydride, 0.2% by weight of diacrylic acid and 0.1% by weight of phenothiazine. The reaction temperatures in the reactors were 107° C., 118° C. and 125° C., and the pressure was 700 mbar. A mixture of water, n-butanol, n-butyl acrylate, n-butyl acetate and dibutyl ether was obtained at the top of the column and separated into an aqueous phase and an organic phase. The aqueous phase was discharged and, apart from the discharged fraction (see below), the organic phase was recycled as reflux to the column. 25 g per hour of the organic phase, mainly comprising 24% by weight of n-butyl acrylate, 54% by weight of n-butanol, 8% by weight of n-butyl acetate and 2% by weight of dibutyl ether, were discharged. The column was stabilized by adding 30 g of a 1% strength phenothiazine solution in n-butyl acrylate to the uppermost tray. The condensate was stabilized by applying 50 ml of a 1% strength aqueous solution of 4-hydroxy-2,2,6,6-tetramethylpiperidin-N-oxyl to the condenser. The reactor discharge (1280 g/h) still contained 0.6% by weight of acrylic acid, and the acrylic acid conversion was 98.0%.

The reactor discharge cooled to about 25° C. was washed in one-stage mixer-settler apparatuses with a 6% strength by weight sodium hydroxide solution (200 ml/h) and with water (100 ml/h) to separate off acid.

The substantially acid-free organic phase was separated into a low boiler fraction and a bottom product, which mainly contained n-butyl acrylate and high boilers, in a distillation unit consisting of a circulation evaporator, a column having 40 bubble trays, a condenser and a phase separation vessel. 107 g of the low boiler fraction, mainly comprising butyl acrylate (63.6% by weight), butyl acetate (1.3% by weight), butanol (26% by weight) and dibutyl ether (0.5% by weight), were recycled into the esterification cascade. The reflux ratio was 10. The bottom temperature was 107° C. and the top temperature was 80° C. at 175 mbar. The distillation unit was stabilized by applying 50 g of 1% strength by weight solution of phenothiazine in n-butyl acrylate to the condenser.

In a further distillation unit consisting of a circulation evaporator, a dual-flow column (30 trays) and a condenser, n-butyl acrylate in a purity of 99.9% was separated from the bottom product (yield 95%). The feed was effected on the 10th tray, the bottom temperature was 110° C. and the top temperature was 80° C. at 105 mbar. The column was stabilized with 0.1% strength by weight hydroquinone monomethyl ether in n-butyl acrylate via the reflux (15 ppm of hydroquinone monomethyl ether, reflux ratio 0.4) and by adding a 1% strength by weight solution of hydroquinone monomethyl ether in n-butyl acrylate to the 15th tray.

The aqueous phases obtained on separating off acid were combined, acidified (pH 1) with concentrated sulfuric acid and extracted with a mixture of 120 g/h of distillate from the transesterification analogous to example 1 and 80 g of n-butyl acrylate in a three-stage mixer-settler apparatus. The acrylic acid-containing organic phase in which no dimethylaminoethanol was detectable (3% by weight of acrylic acid) was recycled to the first esterification reactor.

The esterification could be operated without problems for at least 500 hours without dimethylaminoethyl acrylate being detectable in the product.

We claim:
1. A process for the preparation of higher (meth)acrylates by transesterification of a lower (meth)acrylate with a higher alcohol $R^2OH$ which either carries, as $R^2$, $C_2$–$C_{12}$-alkyl radical having at least one $NR^3{}_2$ group in which $R^3$ is $C_1$–$C_6$-alkyl and N may also be a member of a five- to seven-membered ring or is $R^3{}_2N(-CH_2CH_2-O)y$-H, $R^3{}_2N(-CH(CH_3)-CH-O)_y$-H or $R^3{}_2N(-CH_2CH(CH_3)-O)_y$-H, where y is an integer from 1 to 4, in the presence of a stabilizer or stabilizer mixture and of a catalyst or catalyst mixture, wherein the liberated lower alkanol $R^1OH$, where $R^1$ contains at least 1 carbon atom less than $R^2$, is separated off and is fed at least partly to the preparation of a lower (meth)acrylate without further purification.

2. A process for the preparation of higher (meth)acrylates by transesterification of a lower (meth)acrylate with a higher alcohol $R^2OH$ which is selected from 2-(dimethylamino) ethanol, 3-(dimethylamino)propanol, 4-(dimethylamino)butanol, 5-(dimethylamino)pentanol, 6-(dimethylamino)hexanol, 8-(dimethylamino)octanol, 10-(dimethylamino)decanol, 12-(dimethylamino)dodecanol, 2-(diethylamino)ethanol, 3-(diethylamino)propanol, 4-(diethylamino)butanol, 5-(diethylamino)pentanol, 6-(diethylamino)hexanol, 8-(diethylamino)octanol, 10-(diethylamino)decanol, 12-(diethylamino)dodecanol, 2-(di(isopropyl)amino)ethanol, 3-(di(isopropyl)amino)propanol, 4-(di(isopropyl)amino)-butanol, 5-(di(isopropyl)amino)pentanol, 6-(di(isopropyl)amino)hexanol, 8-(di(isopropyl)amino)octanol, 10-(di(isopropyl)amino)decanol, 12-(di(isopropyl)amino)-dodecanol, 2-(dibutylamino)ethanol, 3-(dibutylamino)propanol, 4-(dibutylamino)butanol, 5-(dibutylamino)pentanol, 6-(dibutylamino)hexanol, 8-(dibutylamino)octanol, 10-(dibutylamino)decanol, 12-(dibutylamino)dodecanol, 2-(dihexylamino)ethanol, 3-(dihexylamino)propanol, 4-(dihexylamino)butanol, 5-(dihexylamino)pentanol, 6-(dihexylamino)hexanol, 8-(dihexylamino)octanol, 10-(dihexylamino)decanol, 12-(dihexylamino)dodecanol, 2-(methylethylamino)ethanol, 2-(methylpropylamino)ethanol, 2-(methylisopropylamino)-ethanol, 2-(methylbutylamino)ethanol, 2-(methylhexylamino)ethanol, 2-(methyloctylamino)ethanol, 2-(ethylpropylamino)ethanol, 2-(ethylisopropylamino)ethanol, 2-(ethylbutylamino)ethanol, 2-(ethylhexylamino)ethanol, 2-(ethyloctylamino)ethanol, 3-(methylethylamino)propanol, 3-(methylpropylamino)propanol, 3-(methylisopropylamino)-propanol, 3-(methylbutylamino)propanol, 3-(methylhexylamino)-propanol, 3-(methyloctylamino)propanol, 3-(ethylpropylamino)-propanol, 3-ethylisopropylamino)propanol, 3-(ethylbutylamino)propanol, 3-(ethylhexylamino)propanol, 3-(ethyloctylamino)propanol, 4-(methylethylamino)butanol, 4-(methylpropylamino)butanol, 4-(methylisopropylamino)-butanol, 4-(methylbutylamino)butanol, 4-(methylhexylamino)butanol, 4-(methyloctylamino)butanol, 4-(ethylpropylamino)butanol, 4-(ethylisopropylamino)butanol, 4-(ethylbutylamino)butanol, 4-(ethylhexylamino)butanol, 4-(ethyloctylamino)butanol, 2-(N-piperidinyl)ethanol, 3-(N-piperidinyl)propanol, 4-(N-piperidinyl)butanol, 5-(N-piperidinyl)pentanol, 6-(N-piperidinyl)hexanol, 8-(N-piperidinyl)octanol, 10-(N-piperidinyl)decanol, 12-(N-piperidinyl)dodecanol, 2-(N-pyrrolidinyl)ethanol, 3-(N-pyrrolidinyl)propanol, 4-(N-pyrrolidinyl)butanol, 5-(N-pyrrolidinyl)pentanol, 6-(N-pyrrolidinyl)hexanol, 8-(N-pyrrolidinyl)octanol, 10-(N-pyrrolidinyl)decanol, 12-(N-pyrrolidinyl)dodecanol, 2-(N-morpholino)ethanol, 3-(N-morpholino)propanol, 4-(N-morpholino)butanol, 5-(N-morpholino)pentanol, 6-(N-morpholino)hexanol, 8-(N-morpholino)octanol, 10-(N-morpholino)decanol, 12-(N-morpholino)dodecanol, 2-(N'-methyl-N-piperazinyl)-ethanol, 3-(N'-methyl-N-piperazinyl)propanol, 4-(N'-methyl-N-piperazinyl)butanol, 5-(N'-methyl-N-piperazinyl)pentanol, 6-(N'-methyl-N-piperazinyl)hexanol, 8-(N'-methyl-N-piperazinyl)octanol, 10-(N'-methyl-N-piperazinyl)decanol 12-(N'-methyl-N-piperazinyl)-dodecanol, 2-(N'-ethyl-N-piperazinyl)ethanol, 3(N'-ethyl-N-piperazinyl)propanol, 4-(N'-ethyl-N-piperazinyl)butanol, 5-(N'-ethyl-N-piperazinyl)pentanol, 6-(N'-ethyl-N-piperazinyl)hexanol, 8-(N'-ethyl-N-piperazinyl)octanol, 10-(N'-ethyl-N-piperazinyl)decanol, 12-(N'-ethyl-N-piperazinyl)dodecanol, 2-(N'-isopropyl-N-piperazinyl)ethanol, 3-(N'-isopropyl-N-piperazinyl)-propanol, 4-(N'-isopropyl-N-piperazinyl)butanol, 5-(N'-isopropyl-N-piperazinyl)pentanol, 6-(N'-isopropyl-N-piperazinyl)hexanol, 8-(N'-isopropyl-N-piperazinyl)octanol, 10-(N'-isopropyl-N-piperazinyl)decanol, 12-(N'-isopropyl-N-piperazinyl)dodecanol or ethoxylated and/or propoxylated alcohols and mixed ethoxylated/propoxylated amino alcohols, $R^3{}_2N(-CH_2CH_2-O)_y$-H or $R^3{}_2N(-CH(CH_3)-CH_2-O)_y$-H or $R^3{}_2N(-CH_2-CH(CH_3)-O-)_y$-H, where y is an integer from 1 to 4, in the presence of a stabilizer or stabilizer mixture and of a catalyst or catalyst mixture, wherein the liberated lower alkanol $R^1OH$, which is selected from methanol, ethanol, n-propanol, isopropanol, n-butanol, isobutanol, 2-butanol and tert-butanol, is separated off and is fed at least partly to the preparation of a lower (meth)acrylate without further purification.

3. A process as claimed in claim 2, wherein the higher alcohol is selected from dimethylaminoethanol, diethylaminoethanol, di-n-butylaminoethanol, 3-dimethylaminopropanol, 3-diethylaminopropanol and 3-di-n-butylaminopropanol.

4. A process as claimed in claim 1, wherein the liberated lower alkanol $R^1OH$ is separated off and is fed at least partly to a working-up process in the preparation of the lower (meth)acrylate.

5. A process as claimed in claim 1, wherein the lower alkanol $R^1OH$ is separated off by distillation.

6. A process as claimed in claim 1, wherein the lower alkanol $R^1OH$ liberated during the transesterification is separated off substantially together with lower (meth)acrylate and any higher alcohol $R^2OH$.

7. A process as claimed in claim 1, wherein the mixture liberated during the transesterification, separated off and containing lower alkanol $R^1OH$ is brought into contact with a (meth)acrylic acid-containing stream in a working-up process in the preparation of the lower (meth)acrylate.

8. A process as claimed in claim 7, wherein the mixture liberated during the transesterification, separated off and containing lower alkanol $R^1OH$ is used in a working-up process in the preparation of the lower (meth)acrylate for an extraction of (meth)acrylic acid.

9. A process as claimed in claim 7, wherein the mixture liberated during the transesterification, separated off and containing lower alkanol $R^1OH$ is used in the working-up process in the preparation of a lower (meth)acrylate for an extraction of (meth)acrylic acid from acidified washwater.

10. A process as claimed in claim 8, wherein the extraction is carried out countercurrently.

11. A process as claimed in claim 1, which is carried out continuously.

12. A process as claimed in claim 1, wherein the lower alkanol $R^1OH$ is n-butanol and the lower (meth)acrylate is n-butyl (meth)acrylate.

13. A process as claimed in claim 1, wherein the higher alkanol $R^2OH$ is 2-(N,N-dimethylamino)ethanol and the higher (meth)acrylate is 2-(N,N-dimethylamino)ethyl (meth)acrylate.

14. A process as claimed in claim 2, wherein the liberated lower alkanol $R^1OH$ is separated off and is fed at least partly to a working-up process in the preparation of the lower (meth)acrylate.

15. A process as claimed in claim 2, wherein the lower alkanol $R^1OH$ is separated off by distillation.

16. A process as claimed in claim 2, wherein the lower alkanol $R^1OH$ liberated during the transesterification is separated off substantially together with lower (meth)acrylate and any higher alcohol $R^2OH$.

17. A process as claimed in claim 2, wherein the mixture liberated during the transesterification, separated off and containing lower alkanol $R^1OH$ is brought into contact with a (meth)acrylic acid-containing stream in a working-up process in the preparation of the lower (meth)acrylate.

18. A process as claimed in claim 17, wherein the mixture liberated during the transesterification, separated off and containing lower alkanol $R^1OH$ is used in a working-up process in the preparation of the lower (meth)acrylate for an extraction of (meth)acrylic acid.

19. A process as claimed in claim 17, wherein the mixture liberated during the transesterification, separated off and containing lower alkanol $R^1OH$ is used in a working-up process in the preparation of the lower (meth)acrylate for an extraction of (meth)acrylic acid from acidified washwater.

20. A process as claimed in claim 18, wherein the extraction is carried out countercurrently.

21. A process as claimed in claim 2, which is carried out continuously.

22. A process as claimed in claim 2, wherein the lower alkanol $R^1OH$ is n-butanol and the lower (meth)acrylate is n-butyl (meth)acrylate.

23. A process as claimed in claim 2, wherein the higher alkanol $R^2OH$ is 2-(N,N-dimethylamino)ethanol and the higher (meth)acrylate is 2-(N,N-dimethylamino)ethyl (meth)acrylate.

24. A process for the preparation of higher (meth)acrylates by transesterification of a lower (meth)acrylate with a higher alcohol $R^2OH$ which either carries, as $R^2$, a $C_2$–$C_{12}$-alkyl radical having at least one $NR^3_2$ group in which $R^3$ is $C_1$–$C_6$-alkyl and N may also be a member of a five- to seven-membered ring or is $R^3_2N(-CH_2CH_2-O)y$-H, $R^3_2N(-CH(CH_3)-CH-O)_y$-H or $R^3_2N(-CH_{12}CH(CH_3)-O)_y$13 H, where y is an integer from 1 to 4, in the presence of a stabilizer or stabilizer mixture and of a catalyst or catalyst mixture, wherein the liberated lower alkanol $R^1OH$, where $R^1$ contains at least 1 carbon atom less than $R^2$, is separated off and is fed at least partly to the preparation of a lower (meth)acrylate without further purification over ion-exchange resin.

* * * * *